US010238253B2

(12) United States Patent
Morrow et al.

(10) Patent No.: US 10,238,253 B2
(45) Date of Patent: Mar. 26, 2019

(54) SOLID FRAGRANCE CARRIER AND METHOD OF USE IN A VACUUM CLEANER

(71) Applicant: BISSELL Homecare, Inc., Grand Rapids, MI (US)

(72) Inventors: Nickolas James Morrow, Grand Rapids, MI (US); Michael R. Foote, Ada, MI (US)

(73) Assignee: BISSELL Homecare, Inc., Grand Rapids, MI (US)

( * ) Notice: Subject to any disclaimer, the term of this patent is extended or adjusted under 35 U.S.C. 154(b) by 1444 days.

(21) Appl. No.: 13/961,213

(22) Filed: Aug. 7, 2013

(65) Prior Publication Data

US 2014/0041525 A1     Feb. 13, 2014

Related U.S. Application Data

(60) Provisional application No. 61/680,880, filed on Aug. 8, 2012.

(51) Int. Cl.

| | |
|---|---|
| *B01D 29/05* | (2006.01) |
| *A47L 7/04* | (2006.01) |
| *A47L 9/12* | (2006.01) |
| *A47L 9/14* | (2006.01) |
| *A61L 9/012* | (2006.01) |
| *B01D 46/00* | (2006.01) |
| *B01D 46/10* | (2006.01) |

(52) U.S. Cl.
CPC .............. *A47L 7/04* (2013.01); *A47L 9/122* (2013.01); *A47L 9/14* (2013.01); *A61L 9/012* (2013.01); *B01D 29/05* (2013.01); *B01D 46/0038* (2013.01); *A61L 2209/14* (2013.01); *B01D 46/10* (2013.01)

(58) Field of Classification Search
CPC ..... A47L 7/04; A47L 9/01; A47L 9/14; A47L 9/122; A47L 9/127; A47L 9/1608; A47L 9/1666; B01D 29/01; B01D 29/05; B01D 29/0093; B01D 29/44
USPC ........... 55/502, 511, DIG. 2, DIG. 3; 96/222
See application file for complete search history.

(56) References Cited

U.S. PATENT DOCUMENTS

| | | |
|---|---|---|
| 3,274,758 A | 9/1966 | Parman |
| 4,227,953 A * | 10/1980 | Wasielewski .......... B01D 46/12 156/227 |
| 4,512,788 A | 4/1985 | Weinstein |
| 4,563,333 A | 1/1986 | Frigon |
| 4,831,685 A | 5/1989 | Bosyj et al. |

(Continued)

FOREIGN PATENT DOCUMENTS

| | | |
|---|---|---|
| CA | 2568390 A1 | 12/2005 |
| CA | 2632651 A1 | 6/2007 |

(Continued)

OTHER PUBLICATIONS

Thorsten Sembritzki, European Search Report, dated Oct. 28, 2015, 6 pages, Munich.

(Continued)

*Primary Examiner* — Robert A Hopkins
(74) *Attorney, Agent, or Firm* — McGarry Bair PC

(57) ABSTRACT

A solid fragrance carrier comprising a fragrance-containing polymeric matrix adhesively bonded to a filter or filter bag for filtering an air stream in a vacuum cleaner for providing a fragranced scent to air exhausted from the vacuum cleaner.

12 Claims, 6 Drawing Sheets

(56) References Cited

U.S. PATENT DOCUMENTS

| | | |
|---|---|---|
| 4,858,758 A | 8/1989 | Mitchell et al. |
| 4,865,759 A | 9/1989 | Coyne et al. |
| 5,080,702 A | 1/1992 | Bosses |
| 5,089,167 A | 2/1992 | Coyne et al. |
| 5,104,427 A | 4/1992 | Riley et al. |
| 5,150,791 A | 9/1992 | Kamen et al. |
| 5,181,946 A | 1/1993 | Bosses et al. |
| 5,211,874 A | 5/1993 | Haendler et al. |
| 5,244,703 A | 9/1993 | Bosses |
| 5,283,061 A | 2/1994 | Kamen et al. |
| 5,306,534 A | 4/1994 | Bosses |
| 5,342,420 A | 8/1994 | Bosses |
| 5,461,751 A | 10/1995 | Sepke |
| 5,464,460 A | 11/1995 | Bosses |
| 5,511,278 A | 4/1996 | Shorthill |
| 5,529,781 A | 6/1996 | Kamen et al. |
| 5,547,636 A * | 8/1996 | Vick ................ A61L 9/042 239/60 |
| 5,613,989 A | 3/1997 | Bosses |
| D383,881 S | 9/1997 | Gudmundsson |
| 5,688,298 A | 11/1997 | Bosses |
| 5,690,711 A | 11/1997 | Bosses |
| 5,698,166 A | 12/1997 | Vick et al. |
| D389,284 S | 1/1998 | Gudmundsson |
| 5,772,712 A | 1/1998 | Perea et al. |
| 5,725,620 A | 3/1998 | Perea et al. |
| 5,725,623 A | 3/1998 | Bowerman et al. |
| 5,733,351 A | 3/1998 | Hult et al. |
| 5,827,913 A | 10/1998 | Baetzold et al. |
| 5,861,128 A | 1/1999 | Vick et al. |
| D425,270 S | 5/2000 | Zahuranec |
| 6,063,171 A | 5/2000 | Moyher, Jr. et al. |
| 6,086,649 A | 7/2000 | Tuvin et al. |
| 6,171,375 B1 | 1/2001 | Howie |
| D441,155 S | 4/2001 | Thur et al. |
| 6,290,761 B2 | 9/2001 | Rohn et al. |
| 6,341,404 B1 | 1/2002 | Salo et al. |
| 6,375,720 B2 | 4/2002 | Embree et al. |
| 6,379,408 B1 | 4/2002 | Embree et al. |
| D458,670 S | 6/2002 | Bosyi et al. |
| 6,709,495 B1 | 3/2004 | Storer |
| D494,329 S | 8/2004 | Thur et al. |
| 6,829,804 B2 | 12/2004 | Sepke |
| 6,913,635 B2 | 7/2005 | Yoo et al. |
| D518,257 S | 3/2006 | Seon |
| 7,148,284 B2 | 12/2006 | Morrison et al. |
| 7,201,786 B2 | 4/2007 | Wegelin et al. |
| 7,247,182 B2 | 7/2007 | Boyer, Jr. et al. |
| 7,267,704 B2 | 9/2007 | Allgeier |
| D568,014 S | 4/2008 | Fester et al. |
| 7,357,823 B1 | 4/2008 | Streciwilk |
| 7,374,594 B2 | 5/2008 | Gierer |
| 7,494,520 B2 | 2/2009 | Nam et al. |
| 7,552,506 B2 | 6/2009 | Lee et al. |
| D601,318 S | 9/2009 | Williams et al. |
| D601,319 S | 9/2009 | Williams et al. |
| D601,320 S | 9/2009 | Williams et al. |
| 7,615,109 B2 * | 11/2009 | Sepke ................ A47L 7/04 55/376 |
| D617,064 S | 6/2010 | Hengvoss et al. |
| D617,065 S | 6/2010 | Williams et al. |
| 7,754,198 B2 | 7/2010 | Whitehead et al. |
| 7,799,107 B2 | 9/2010 | Corney et al. |
| 7,837,772 B2 | 11/2010 | Sepke |
| 7,850,038 B2 | 12/2010 | Mueller et al. |
| 7,900,316 B2 | 3/2011 | Fester et al. |
| 7,951,230 B2 | 5/2011 | Sepke |
| 8,043,606 B2 | 10/2011 | MacBeath et al. |
| 2002/0197187 A1 | 12/2002 | Murray |
| 2003/0097936 A1 | 5/2003 | Maleeny et al. |
| 2003/0105183 A1 | 6/2003 | Sharak |
| 2004/0148914 A1 | 8/2004 | Lim et al. |
| 2005/0003197 A1 | 1/2005 | Good et al. |
| 2005/0032963 A1 | 1/2005 | Harwell et al. |
| 2005/0169813 A1 * | 8/2005 | D'Amico ................ A61L 9/042 422/124 |
| 2005/0217067 A1 | 10/2005 | Rew et al. |
| 2005/0272878 A1 | 12/2005 | Corzani et al. |
| 2006/0005711 A1 * | 1/2006 | Olefson ................ A61L 9/042 96/222 |
| 2006/0249592 A1 | 11/2006 | Burrowes et al. |
| 2006/0252327 A1 | 11/2006 | Uitenbroek et al. |
| 2006/0272508 A1 * | 12/2006 | Hoke ................ B01D 53/0415 96/134 |
| 2007/0108759 A1 | 5/2007 | D'Amico |
| 2007/0114142 A1 | 5/2007 | Sine et al. |
| 2008/0132625 A1 | 6/2008 | Niehaus et al. |
| 2010/0011532 A1 | 1/2010 | Norton et al. |
| 2011/0016662 A1 | 1/2011 | Horne |
| 2011/0042257 A1 | 2/2011 | Mueller et al. |
| 2011/0155609 A1 | 6/2011 | Mueller et al. |
| 2012/0010122 A1 | 1/2012 | MacBeath et al. |

FOREIGN PATENT DOCUMENTS

| | | | |
|---|---|---|---|
| CN | 2225292 Y | 4/1996 | |
| CN | 101193688 A | 6/2008 | |
| CN | 102202551 A | 9/2011 | |
| DE | 10209298 A1 | 9/2003 | |
| DE | 102005047704 A1 | 4/2007 | |
| EP | 0809963 A2 | 12/1997 | |
| EP | 0860138 A1 | 8/1998 | |
| EP | 1505138 A2 | 9/2005 | |
| EP | 1604690 A1 | 12/2005 | |
| EP | 1795556 A1 | 6/2007 | |
| GB | 2265096 A | 9/1993 | |
| GB | 2336766 A | 11/1999 | |
| JP | 02051593 | 2/1990 | |
| JP | 05103936 A * | 4/1993 | ............ B01D 46/52 |
| KR | 100259289 B | 6/2000 | |
| WO | 199009813 A1 | 9/1990 | |
| WO | 2000064320 A1 | 11/2000 | |
| WO | 2001078571 A1 | 10/2001 | |
| WO | 2005051155 A1 | 6/2005 | |
| WO | 2005123150 A1 | 12/2005 | |
| WO | 2007062471 A1 | 6/2007 | |
| WO | 2007066280 A2 | 6/2007 | |
| WO | 2008102316 A1 | 8/2008 | |
| WO | 2009021812 A1 | 2/2009 | |

OTHER PUBLICATIONS

Notification of First Office Action, 8 pages, dated Sep. 12, 2016, State Intellectual Property Office of the People's Republic of China.

European Office Action—Communication pursuant to Article 94(3) EPC, 5 pages dated Jun. 20, 2018.

* cited by examiner

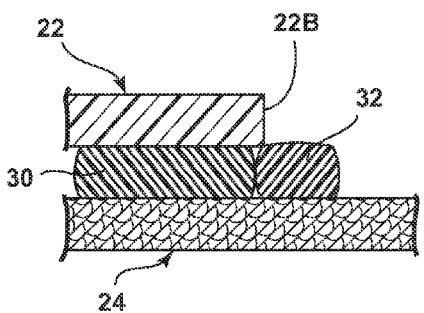
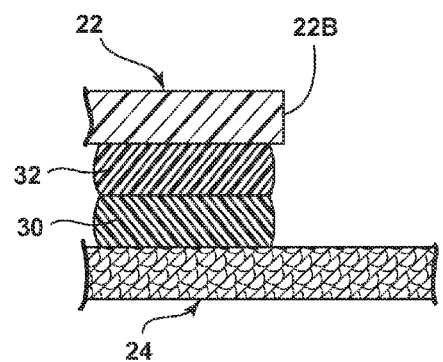
FIG. 3A  FIG. 3B
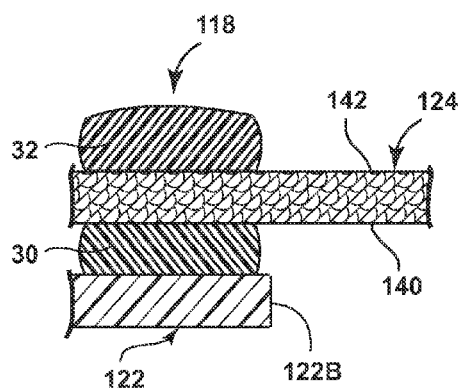
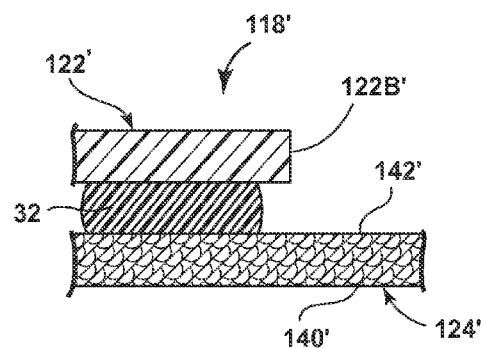
FIG. 4A  FIG. 4B

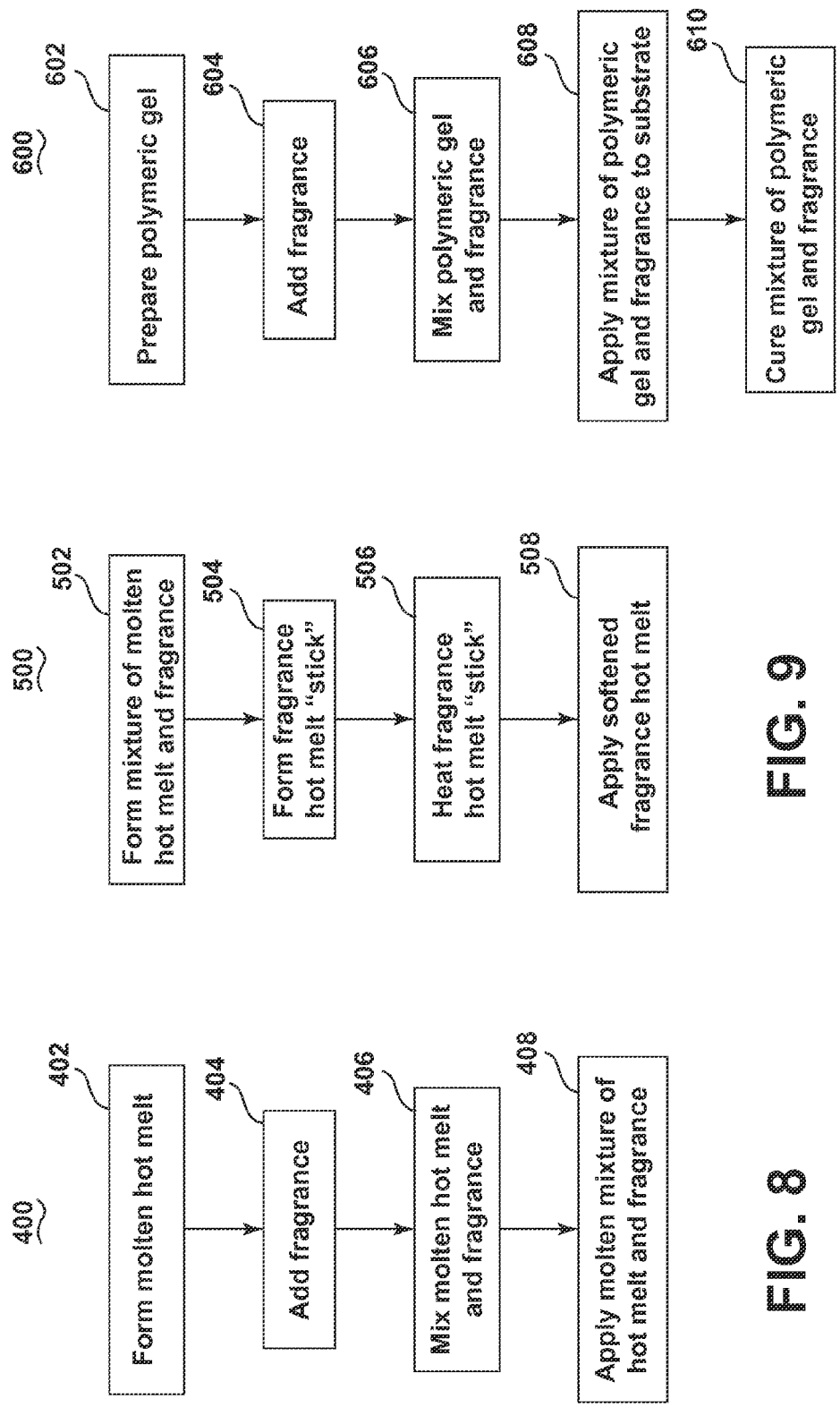

SOLID FRAGRANCE CARRIER AND METHOD OF USE IN A VACUUM CLEANER

CROSS-REFERENCE TO RELATED APPLICATION

This application claims the benefit of U.S. Provisional Patent Application No. 61/680,880, filed Aug. 8, 2013, which is incorporated herein by reference in its entirety.

BACKGROUND

Vacuum cleaners are well-known household cleaning devices that are used to clean dirt and debris from rugs, carpets, floors and other surfaces. Vacuum cleaners typically use a motor/fan assembly for generating suction to draw air and debris into the vacuum cleaner, a filtration and/or separation assembly for separating dirt and debris from the air drawn into the vacuum cleaner by suction force and a collection chamber for collecting and storing the separated dirt and debris for later disposal. Some types of vacuum cleaners use disposable bag filters to collect debris drawn into the vacuum cleaner. The debris-laden air is drawn into the bag, where it is collected and stored, and the relatively clean air exits through the porous walls of the bag to the surrounding environment.

Other types of vacuum cleaners, sometimes referred to as bagless cleaners, may employ a debris collection container or cup to collect debris drawn into the vacuum cleaner, which can be removed to dispose of the collected debris and replaced onto the vacuum cleaner. One or more cyclonic separators can be provided to separate the debris from the air and deposit the debris in the collection container. Particulate filters can be provided on the intake side and/or the outlet side of a suction motor to further filter the air before the air is exhausted to the surrounding environment.

Some vacuum cleaners include a fragrance or deodorizing element to provide a fragrance or deodorize the air that is drawn into and exhausted from the vacuum cleaner during use. For example, U.S. Pat. Nos. 7,837,772 and 7,951,230 to Sepke discloses a variety of filter assemblies for a vacuum cleaner that include sodium bicarbonate or other material, such as a fragrance, for deodorizing the air flowing through the vacuum cleaner in both bagless vacuum cleaners and vacuum cleaners which include bag filters. In the context of a vacuum cleaner which uses a filter bag, an air-pervious sachet filled with sodium bicarbonate can be placed within the filter bag, on the outside of the filter bag or within the filter bag compartment. In another example, deodorant sheets with a sodium bicarbonate mixture impregnated in a single sheet or pressed between two air permeable sheets can be placed inside or adhesively bonded to the inner surface of the bag. Alternatively, a slurry of sodium bicarbonate can be printed or painted onto the filter bag material or provided in powdered form between layers of the filter bag.

In the context of a bagless vacuum cleaner in which debris is collected in a cup, the Sepke patents disclose forming the sodium bicarbonate into solid structures, such as a sleeve that fits into an air conduit, or other structure provided in a dirt cup assembly through which air flows in the vacuum cleaner, such as an air deflector. In another example, sodium bicarbonate can be impregnated into the filter material of a pleated filter or painted or printed onto the filter material of a pleated filter through which air passes on its way to the vacuum motor. In yet another example, the vacuum cleaner can include a filter frame which is connected to a deodorizer chamber which can be filled with deodorizer pellets.

U.S. Pat. No. 5,342,420 to Bosses and U.S. Pat. No. 3,274,758 to Parman disclose filter bags which can include a deodorizing material. The Bosses '420 patent discloses a porous substrate having an active agent thereon or therein that can be adhesively secured to the outer surface of the filter bag. The active agent can be an ingredient, such as an essential oil, that re-odorizes or deodorizes the air passing through the filter paper of the filter bag. The Parman '758 patent discloses a filter bag in which an envelope filled with a deodorizing material is provided at the inlet opening of the filter bag. The envelope is ruptured when the exhaust conduit is inserted through the inlet opening of the filter bag and the deodorant particles are released into the filter bag.

Devices can also be used to provide a deodorizer or fragrance to air flowing through air ventilation systems. For example, U.S. Pat. Nos. 5,547,636, 5,698,166 and 5,861,128 to Vick et al. disclose an air freshening device which includes a fragrant material applied to an air permeable substrate. The fragrant material can be an ethylene vinyl acetate-based hot melt adhesive mixed with a fragrant liquid. The air permeable substrate can then be attached to a filter in a forced air heating, ventilating or cooling system using an attachment device having a barbed shaft which engages the fibers of the filter to hold the substrate against the filter.

Another example of a reference that discloses attaching a fragranced, air permeable structure to an air filter in a ventilation system is U.S. Pat. No. 4,563,333 to Frigon. Frigon '333 discloses a perforated cardboard packet having adhesive-backed tabs for attaching the packet to the corners of a filter. A solid deodorant insert of air freshening material is provided within the packet.

Hot-melt adhesives which include a fragrance have also been used to provide containers with a fragrance. For example, U.S. Pat. No. 4,865,759 to Coyne et al. and U.S. Pat. No. 4,858,758 to Mitchell et al. both disclose an ethylene vinyl acetate-based hot melt adhesive comprising a fragrance for use in the head space of a container, such as a bleach container. U.S. Pat. No. 5,150,791 to Revlon discloses an ethylene vinyl acetate-based hot melt adhesive composition that is provided on a container that includes a color indicative of the color of the cosmetic inside the container, and which can also include a fragrance.

BRIEF SUMMARY

According to an embodiment of the invention, a filter for filtering an air stream in a vacuum cleaner, the vacuum cleaner having a suction source for drawing an airstream from a surface to be cleaned to a debris collector for collecting dirt and debris carried by the airstream, comprises a frame with an edge defining an open area through which air may pass, a filter media mounted to the frame and covering the open area, and a fragrance-containing polymeric matrix adhesively bonded to at least one of the frame or to the filter media adjacent the edge of the frame.

According to another embodiment of the invention, the filter can include one or more of the following additional features: the fragrance-containing polymeric matrix can be adhesively bonded directly to the frame; the filter media can be adhesively bonded to the frame by the fragrance-containing polymeric matrix; the fragrance-containing polymeric matrix can be adhesively bonded to the filter media and to the frame; the fragrance-containing polymeric matrix can be adhesively bonded to the filter media adjacent the frame; and the fragrance-containing polymeric matrix forms a bead around at least a portion of the edge of the frame.

According to yet another embodiment, the fragrance-containing polymeric matrix comprises at least one of a hot melt adhesive or a wax which is applied to the filter in a liquid form and solidifies upon curing. In another embodiment, the fragrance-containing polymeric matrix comprises a polymeric gel which is applied to the filter in a liquid form and solidifies upon curing.

According to another embodiment of the invention, a filter bag for use in a vacuum cleaner, the vacuum cleaner having a suction source for drawing an airstream from a surface to be cleaned to the filter bag for collecting debris carried by the airstream, comprises at least a portion made from a porous material such that dirt and debris entrained in the airstream are filtered out of the air stream and collected within the filter bag as the airstream passes through the filter bag and fragrance-containing polymeric matrix adhesively bonded to the filter bag.

In another embodiment, the fragrance-containing polymeric matrix can be adhesively bonded to the at least a portion of the porous material.

In yet another embodiment, the filter bag further comprises a non-porous portion, and wherein the fragrance-containing polymeric matrix is adhesively bonded to the non-porous portion. The non-porous portion can comprise at least one of a fold or a seam of the filter bag.

According to another embodiment, a method of forming a solid fragrance carrier on a filter element in a vacuum cleaner comprises mixing a liquid polymeric gel with a liquid fragrance to form a fragranced gel, applying the fragranced gel to a filter element for a vacuum cleaner, and curing the fragranced gel to solidify the fragranced gel on the filter element such that the fragranced gel adhesively bonds to the filter element. The filter element can be a filter or a filter bag.

According to yet another embodiment, the mixing can comprise mixing the liquid polymeric gel with the liquid fragrance in a static mixing nozzle.

In another embodiment, curing the fragranced gel comprises at least one of cooling the fragranced gel, applying heat or applying ultraviolet light to the fragranced gel.

BRIEF DESCRIPTION OF THE DRAWINGS

In the drawings:

FIG. 3A is cross-sectional view of a portion of a filter for a vacuum cleaner according to a third embodiment of the invention.

FIG. 3B is cross-sectional view of a portion of a filter for a vacuum cleaner according to a fourth embodiment of the invention.

FIG. 4A is cross-sectional view of a portion of a filter for a vacuum cleaner according to a fifth embodiment of the invention.

FIG. 4B is cross-sectional view of a portion of a filter for a vacuum cleaner according to a sixth embodiment of the invention.

FIG. 8 is a flow chart illustrating a method of forming and applying a solid fragrance carrier for application to a filter or filter bag according to an eleventh embodiment of the invention.

FIG. 9 is a flow chart illustrating a method of forming a solid fragrance carrier for application to a filter or filter bag according to a twelfth embodiment of the invention.

FIG. 10 is a flow chart illustrating a method of forming and applying a solid fragrance carrier for application to a filter or filter bag according to a thirteenth embodiment of the invention.

DETAILED DESCRIPTION

The embodiments of the invention relate to filters for use in upright or canister type vacuums, deep cleaners, sweepers, hand-held vacuum cleaners and any other type of surface cleaner that uses suction to remove debris from a surface being cleaned. The details of the structure of the vacuum cleaner are not germane to the invention and will only be described in such detail as is necessary for a complete understanding of the embodiments of the invention.

Figure 1:
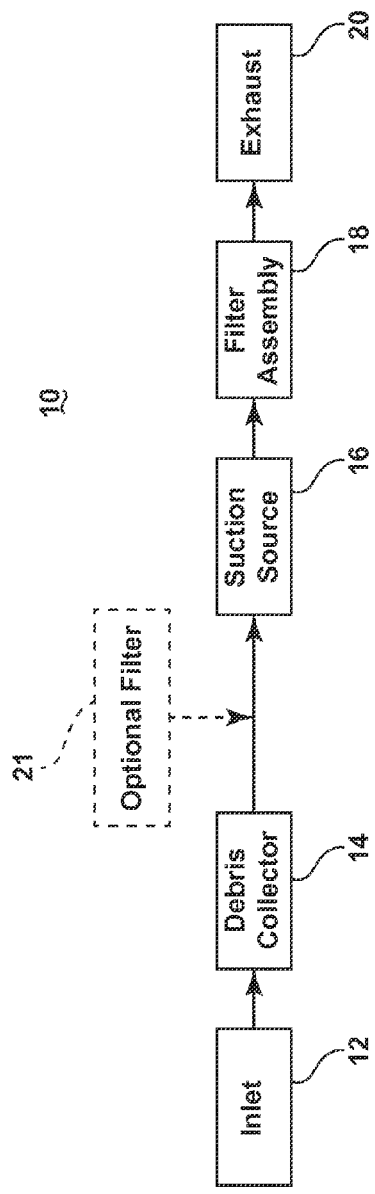
FIG. 1 is a schematic representation of a vacuum cleaner according to a first embodiment of the invention.

FIG. 1 illustrates a schematic of a vacuum cleaner 10 for use according to the embodiments of the invention. The vacuum cleaner 10 includes an inlet 12 through which an airstream comprising dirt, debris and other material present on the surface being cleaned is drawn into the vacuum cleaner as a result of suction applied to the inlet 12 by a suction source 16 such as a motor and fan assembly, for example. The dirty airstream travels from the inlet 12 to a debris collector 14 where the dirt, debris and other material carried by the airstream can be separated from the airstream and collected. The debris can be separated from the airstream using one or more filters and/or cyclone separators, as is known in the art. The at least partially cleaned airstream then travels through a filter 18 where particles still entrained in the airstream can be filtered out of the airstream before the airstream is exhausted through an exhaust 20 to the surrounding environment. The vacuum cleaner 10 can also be provided with one or more optional filters 21 between the debris collector 14 and the suction source 16 to further clean the airstream.

Figure 2:
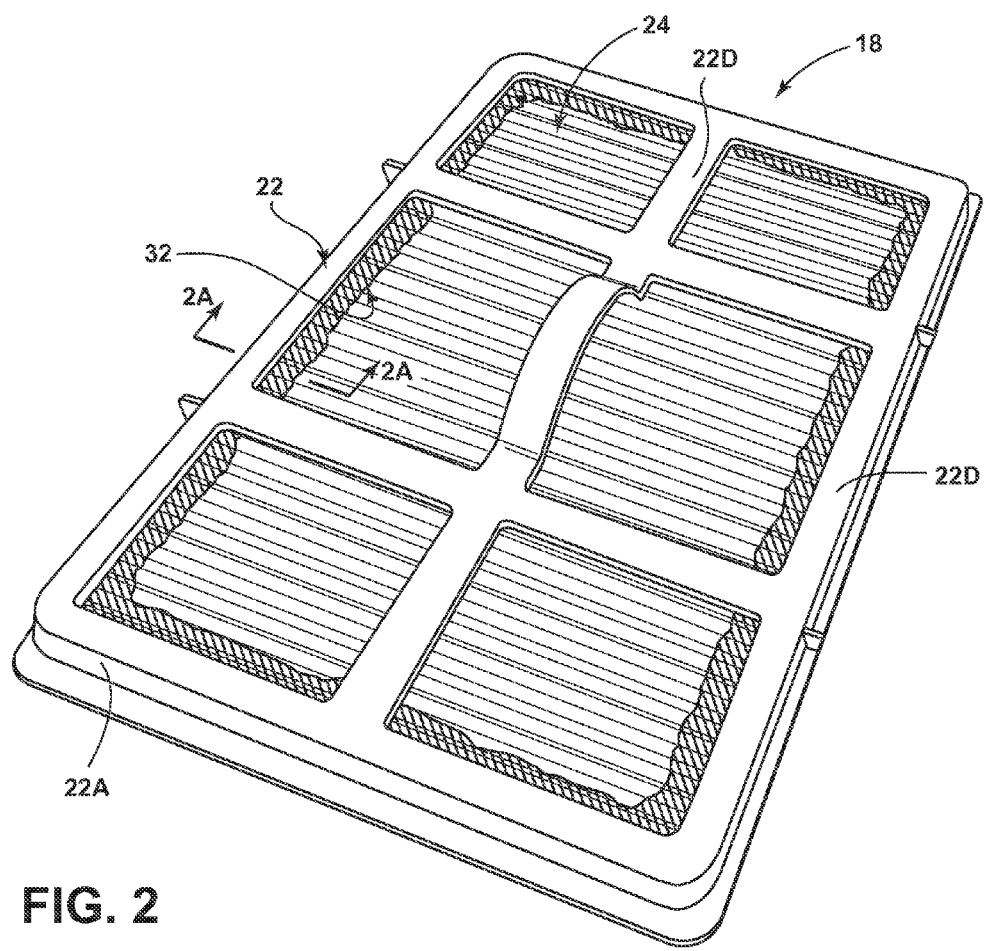
FIG. 2 is a perspective view of a filter for a vacuum cleaner according to a second embodiment of the invention.

Referring now to FIG. 2, an exemplary filter 18 for use with the vacuum cleaner 10 is illustrated. The filter 18 can include a frame 22 which defines an 22C open area through which air may pass and supports a filter media 24. The frame 22 comprises a rectangular rim 22A which may include a flange 22D with an inside edge 22B forming the open area 22C and the filter 24 is mounted in the frame to cover the open area 22C. The flange 22D may partially retain the filter media 24 in the frame and the flange 22D may extend across the open area 22C. While the frame 22 is shown as rectangular, the frame 22 may have different geometric shapes to suit the cross-sectional area in which the filter may be mounted.

The filter media 24 can be any suitable type or combination of types of material suitable for filtering particles entrained within an airstream. Non-limiting examples of filter media 24 include paper, cellulosic material, non-woven material, spunbond material, pleated filter media, open cell foam, polyester type matrix (terylene), bag type paper, bag type non-woven, bag type paper/non-woven and combinations thereof. The filter media 24 can also be a reusable or washable type of media such as a non-woven or foam type filter media, for example. It will be understood that the dimensions of the filter 18 will vary depending on the vacuum cleaner in which the filter 18 is intended for use and that the embodiments of the invention are not limited to any particular vacuum cleaner filter.

Figure 2A:
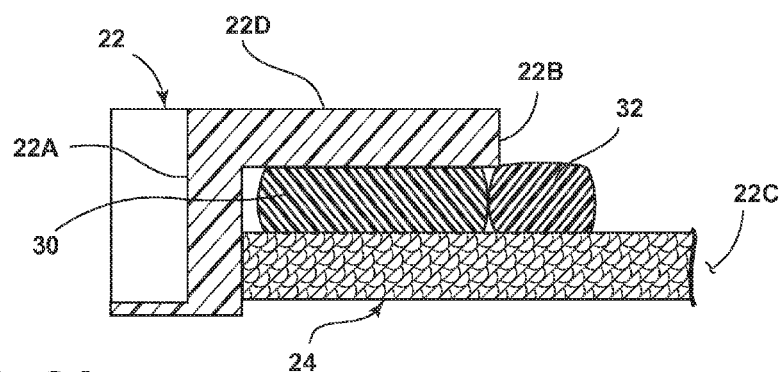
FIG. 2A is a partial cross-sectional view of the filter of FIG. 2 along the line 2A-2A.

As can be seen more clearly in FIG. 2A, the frame 22 can be secured to the filter media 24 by an adhesive 30 applied between the frame 22 and the filter media 24. A solid fragrance carrier 32 can be applied to the filter media 24 adjacent the frame 22 and adhesive 30. As illustrated in FIGS. 2 and 2A, the solid fragrance carrier 32 can extend around the perimeter of the filter media 24 adjacent at least a portion of the flange 22D, thus forming a portion of the frame 22, which, along with the frame 22, can form a frame assembly defining the open area 22C through which air may pass.

FIGS. 3A and 3B schematically illustrate non-limiting alternative locations for applying the solid fragrance carrier 32 relative to the adhesive 30. In the example illustrated in FIG. 3A, the filter media 24 can be secured to the frame 22 using an adhesive 30 and the solid fragrance carrier 32 can be applied to the filter media 24 adjacent the adhesive 30 and adjacent the inside edge 22B of the frame 22. Alternatively, as illustrated in FIG. 3B, the solid fragrance carrier 32 can be applied on top of the adhesive 30 between the frame 22 and the filter media 24. The adhesive 30 and solid fragrance carrier 32 can be provided all the way around the perimeter of the filter media 24, as illustrated in FIG. 2, or only partially around the perimeter. It is also within the scope of the invention for the solid fragrance carrier 32 to be provided at additional locations on the surface of the filter media 24. Non-limiting examples include on the intake side of the filter media 24, the exhaust air side of the filter media 24, on the frame 22, and within the pleats of a pleated filter media.

The adhesive 30 can be any suitable type of adhesive for securing the filter media 24 to the frame 22. One suitable type of adhesive is a hot melt adhesive, such as a hydrocarbon resin available from 3M® (St. Paul, Minn., USA). The hot melt adhesive can be heated to a softened or molten liquid state for application between the frame 22 and the filter media 24. As the hot melt adhesive cools, it solidifies, bonding the frame 22 and the filter media 24. The hot melt adhesive can be applied as a bead or strip and it will be understood that some amount of spreading may occur during application.

The solid fragrance carrier 32 comprises a fragrance suspended or mixed in a polymeric matrix. The polymeric matrix can be applied as a bead or strip and it will be understood that some amount of spreading may occur during application. The polymeric matrix is characterized by an ability to be in a liquid form when heated and/or prior to curing and a solid, adherent form upon curing so that the polymeric matrix adheres to a substrate to which it is applied in liquid form and maintains its shape and form upon curing to a solid form.

As used herein, the term curing refers to the solidifying of a material brought about by chemical additives, ultraviolet or other radiation, heat, pressure, drying, application of water, and/or cooling. In one example, curing may include allowing the polymeric matrix to cool to a predetermined temperature, such as ambient temperature, for example, for a predetermined period of time. Alternatively, or additionally, curing can also include heating to a predetermined temperature or exposure to ultraviolet light for a predetermined period of time. It will be understood by those of ordinary skill in the art that the process for curing a given polymeric material is dependent on the components of the material and may include multiple mechanisms by which the polymeric material may be cured. As used herein, the term "liquid" means the ability of a material to flow and have a definite volume, but no fixed shape. The term "solid" as used herein means the ability of a material to maintain its shape and form upon curing.

The polymeric matrix is a material that can adhesively bond to a substrate and/or adhesively bond two substrates together. As used herein, adhesively bond refers to joining two materials together by mechanical and/or chemical means. For example, the adhesive bond may join two materials together by either or both mechanical mechanisms, such as when the polymeric matrix spreads into the pores in an adjacent substrate, and chemical mechanisms. An adhesive bond can have many forms which involve intermolecular interactions between the adhesive material and an adjacent substrate, non-limiting examples of which include absorption, chemisorption, chemical bonding and/or van der Waals interactions.

Non-limiting examples of suitable polymeric matrices having both the desired liquid and solid characteristics include thermoplastic polymers, such as those used in hot melt applications, natural and synthetic waxes, and polymeric gels. For example, ethylene-vinyl acetate (EVA) polymer is an example of a thermoplastic polymer used in hot melt applications which becomes a molten liquid when heated above its melting temperature and solidifies and adhesively bonds to a substrate upon cooling below its melting temperature.

In one embodiment, the solid fragrance carrier 32 is a fragranced hot melt adhesive comprising a mixture of a fragrance and a hot melt adhesive. The hot melt adhesive may be the same as the adhesive 30 or a different hot melt adhesive. The fragrance can comprise one or more natural or synthetic volatile aroma compounds and can be combined with the hot melt adhesive such that the solidified hot melt emits a desired scent.

For example, the solid fragrance carrier 32 can comprise 80% of a low melting/softening point hot melt adhesive and 20% of a desired fragrance. According to one exemplary embodiment, the solid fragrance carrier can comprise 80% of Scotch-Weld™ Hot Melt Adhesive 3750 (available from 3M®) and 20% Givaudan Floating (available from Procter & Gamble). In another example, the hot melt adhesive can be Scotch-Weld® Hot Melt Adhesive 3748. The ratio of hot melt adhesive to fragrance can vary depending on the properties of the hot melt adhesive and the fragrance, the desired level of scent in the final product, the process in which the hot melt and fragrance mixture is formed and applied, and the vacuum cleaner in which the filter with the fragranced hot melt adhesive is intended for use.

In another embodiment, the solid fragrance carrier 32 can comprise a polymeric gel. The polymeric gel can be selected so as to be compatible with the desired fragrance. In one example, the polymeric gel can be selected to a form a stable material that can comprise 60-80% or more fragrance composition loading with no hysteresis. If the components in the polymeric gel, such as the different fragrance components or the polymeric components, for example, are not balanced properly, the transition from a gel to a solid or the overall stability of solid may be effected. In general, a polymeric gel can be loaded with a higher percentage of fragrance components and still provide a stable gel to solid transition. However, it will be understood that the stability and percent loading capabilities are based on the combination of materials present in the composition.

One example of a suitable polymeric gel is Vapor-Rite Aromatic Gelled Fragrances Concentrates, available from Gelled Fragrance Technologies, LLC. Another example is a polyvinyl chloride-based polymeric gel, such as described in U.S. Pat. No. 7,754,198, issued Jul. 13, 2010, and incorporated herein by reference in full. The high fragrance composition loading available with polymeric gels allows for a smaller amount of the solid fragrance carrier 32 to be used on the filter to achieve the same level of fragrance. This can be beneficial in applications where space for the solid fragrance carrier 32 is limited.

The polymeric matrix can be selected based on the desired properties of the polymeric matrix, which can vary depending on the method of application, the desired fragrance and level of fragrance, and the vacuum cleaner in which the filter 18 is intended for use. For example, in situations where lower heat resistance is suitable, Scotch-Weld® Hot Melt Adhesive 3750 can be used. In situations where higher heat resistance is required, Scotch-Weld® Hot Melt Adhesive 3748 can be used. Hot melt adhesives having a melting temperature in the range of 170-325° F. (77-163° C.), such as ethylene vinyl acetate (EVA), polypropylene (PP) and polyamide (PA) based hot melts are examples of hot melt adhesives suitable for use in the solid fragrance carrier.

The polymeric matrix can also be selected based on its fragrance loading capabilities. Preferably, the polymeric matrix has a fragrance loading capability of at least 10-30% by weight. For example, hot melt adhesives can have a fragrance loading capability of 10-30% by weight, while some gels can have a fragrance loading of up to 80% by weight, with some as high as 85-90% by weight.

When the solid fragrance carrier 32 comprises a hot melt adhesive as the polymeric matrix and is intended for use in a post-motor filter, the hot melt adhesive can be selected so that it is capable of withstanding the exhaust temperatures of the vacuum cleaner motor/fan assembly, which can vary depending on the vacuum cleaner. For example, vacuum cleaners intended for use in European markets typically have a higher wattage motor/fan assembly than vacuum cleaners intended for use in U.S. markets and thus typically have a higher exhaust air temperature. In one example, if the temperature of the motor/fan assembly exhaust during operation is 150° F. (65° C.), a hot melt with a melting temperature above 150° F. (65° C.) can be selected so that the hot melt does not soften or melt and lose its shape during operation of the vacuum cleaner. Preferably the melting temperature of the hot melt will be at least 10° F. (12° C.) above the exhaust temperature.

Many other locations within the vacuum cleaner in which the solid fragrance carrier 32 can be used, such as with a pre-motor filter, experience ambient or close to ambient temperatures and thus the selected hot melt adhesive would need to have a melting temperature above ambient temperatures, preferably at least 10° F. (12° C.) above ambient. Ambient temperatures can vary depending on the weather and the geographic location, for example. In one example, the selection of the hot melt adhesive can be based on an average high temperature for a given region in which the vacuum cleaner is intended for use. Alternatively, the hot melt adhesive can be selected based on a maximum ambient temperature the vacuum cleaner is intended to be used in, such as 120° F. (49° C.), for example.

The solid fragrance carrier 32 can also be colored to provide a visual aid during application and inspection during manufacturing and to provide a visual indicator to the consumer. A suitable dye can be combined with the fragrance, e.g. 0.01% dye, prior to mixing the fragrance with a hot melt adhesive or a polymeric gel, for example. In one example, the fragrance can be blended with a carrier, such as propylene glycol, vegetable oil or mineral oil, or a solvent, and the dye can be blended or dissolved in the carrier or solvent with the fragrance.

The solid fragrance carrier 32 can also include additional additives to provide the desired characteristics during processing, application and after application. Non-limiting examples of additives include tackifiers, waxes, plasticizers, antioxidants, UV stabilizers, biocides, flame retardants, fillers and antistatic agents.

FIGS. 4A and 4B illustrate alternative filters 118 and 118' that may be used with the vacuum cleaner 10 that are similar to the filter 18 except for the location of the adhesive 30 and solid fragrance carrier 32. Therefore, elements of the filter 118 and 118' similar to the filter 18 are labeled with the prefix 100 and 100', respectively.

As illustrated in FIG. 4A, the adhesive 30 can be provided on a first side 140 of the filter media 124 to secure the filter media 124 to the frame 122. The solid fragrance carrier 32 can be provided on a second side 142 of the filter media 124, opposite the first side 140. The first side 140 is the intake side of the filter 118 and the second side 142 is the exhaust air side of the filter 118 such that the airstream enters the filter 118 at the first side 140 and exits at the second side 142. Placing the solid fragrance carrier 32 on the exhaust air side 142 decreases the amount of debris that comes in contact with the solid fragrance carrier 32.

Alternatively, as illustrated in FIG. 4B, the solid fragrance carrier 32, when in the form of a hot melt adhesive, for example, can be used to secure the filter media 124' to the frame 122' without a separate adhesive 30. As illustrated in FIG. 4B, the solid fragrance carrier 32 can be used to secure the filter media 124' to the frame 122' on the second, exhaust air side 142' of the filter 118'.

Figure 5A:
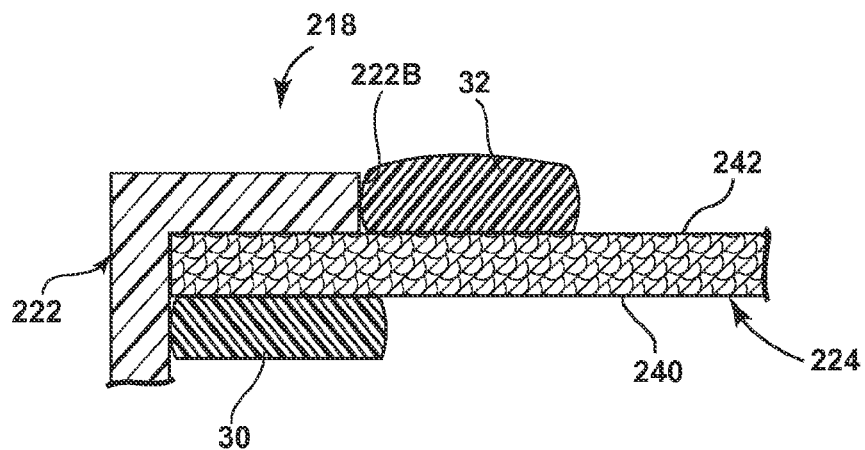
FIG. 5A is cross-sectional view of a portion of a filter for a vacuum cleaner according to a seventh embodiment of the invention.
Figure 5B:
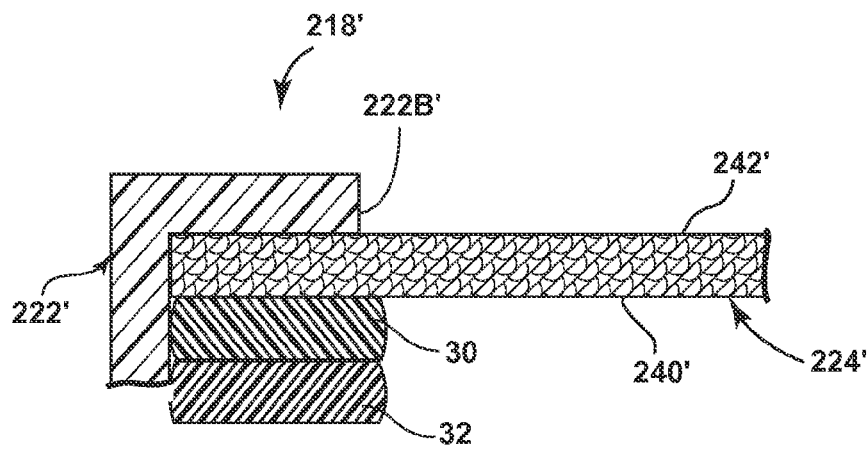
FIG. 5B is cross-sectional view of a portion of a filter for a vacuum cleaner according to an eighth embodiment of the invention.

FIGS. 5A and 5B illustrate additional alternative filters 218 and 218' that may be used with the vacuum cleaner 10 that are similar to the filter 18 except for the location of the adhesive 30 and solid fragrance carrier 32. Therefore, elements of the filter 218 and 218' similar to the filter 18 are labeled with the prefix 200 and 200', respectively.

As illustrated in FIG. 5A, the solid fragrance carrier 32 can be provided on the filter media 224 on the second, exhaust air side 242 of the filter media 224. The filter media 224 can abut the frame 222 on the second, exhaust air side 242 and the adhesive 30 can be provided on the first, intake air side 240 of the filter media 224, adjacent the frame 222. Alternatively, as illustrated in FIG. 5B, both the adhesive 30 and the solid fragrance carrier 32 can be provided on the first, intake air side 240'. The frame 222' can directly abut the filter media 224' on the second, exhaust air side 242'. The adhesive 30 can be provided on the filter media 224' on the first, intake air side 240' adjacent the frame 222'. The solid fragrance carrier 32 can be provided on top of the adhesive 30.

In the embodiments illustrated in FIGS. 2, 2A, 3A, 4A, 5A and 5B, the solid fragrance carrier 32 can be added during or after the filter has already been assembled. In the embodiments illustrated in FIGS. 3B and 4B, the solid fragrance carrier 32 is added during assembly of the filter. Following assembly of the filter and application of the solid fragrance carrier 32, the filters can be sealed inside a plastic bag or container to decrease or prevent release of the fragrance from the solid fragrance carrier 32 during transportation and storage.

Figure 6:
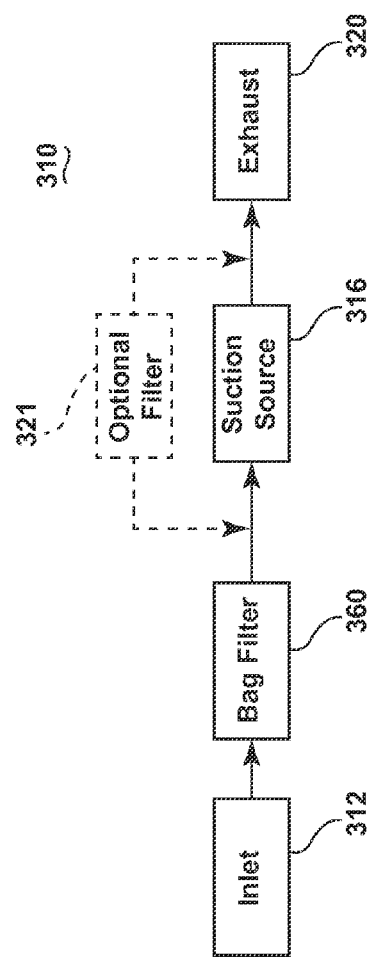
FIG. 6 is a schematic of a vacuum cleaner according to a ninth embodiment of the invention.

Referring now to FIG. 6, a vacuum cleaner 310, similar to the vacuum cleaner 10 of FIG. 1, is schematically illustrated. The vacuum cleaner 310 is similar to the vacuum cleaner 10 except for the debris collector is in the form of a bag filter 360. The bag filter 360 can be at least partially made from a porous material such that dirt and debris entrained in the airstream are filtered out of the airstream and collected within the filter bag 360 as the airstream passes through the bag filter 360. It is also within the scope of the invention for the vacuum cleaner 310 to include additional, optional filters 321, either on the air intake or exhaust side of the suction source 316, as is known in the art.

Figure 7:
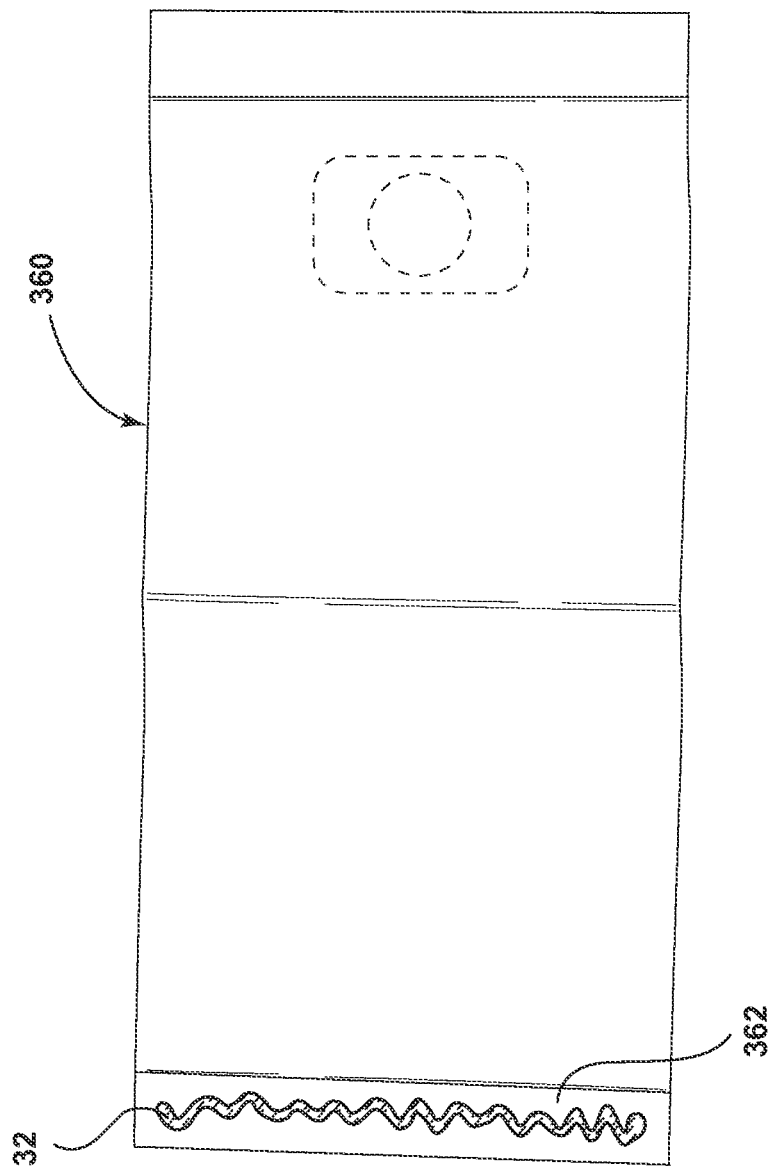
FIG. 7 is a perspective view of a filter bag for a vacuum cleaner according to a tenth embodiment of the invention.

As illustrated in FIG. 7, the solid fragrance carrier 32 can be provided on the bag filter 360. The solid fragrance carrier 32 can be applied on a non-porous portion of the bag filter 360, such as a fold 362, as illustrated, or at any other suitable porous or non-porous location on the bag filter 360, such as a seam. Applying the solid fragrance carrier 32 to a non-porous portion has the advantage of not degrading or interfering with the filter area on the porous portion of the bag filter 360. The solid fragrance carrier 32 can be covered by a strip of removable material (not shown), such as cellophane, releasable tape or paper, for example that can be removed by a user prior to installing the bag filter 360 in the vacuum cleaner 310. In another example, the bag filter 360 can include a support, such as a strip of paper or plastic that is attached to the bag filter 360 and the solid fragrance carrier 32 can be provided on the support.

In use, the volatile fragrance compounds in the solid fragrance carrier 32 applied to the filters 18, 118, 118', 218 and 218' or bag filter 360, will be emitted from the solidified hot melt, wax, or polymeric gel over time. As air flows through the vacuum cleaner 10 or 310, the emitted fragrance will be carried by the airflow as the airflow is exhausted through the filters 18, 118, 118', 218 and 218' or bag filter 360, thus providing the exhaust from the vacuum cleaner with a desired scent.

While the solid fragrance carrier has been described in the context of a post-motor filter or filter bag, it will be understood that the solid fragrance carrier can be used in a similar manner on any filter or multiple filters within a vacuum cleaner.

Referring now to FIG. 8, a flow chart of a method 400 of making and applying a solid fragrance carrier 32 comprising a hot melt adhesive and a fragrance is illustrated. The sequence of steps depicted for this method and the proceeding methods are for illustrative purposes only, and is not meant to limit any of the methods in any way as it is understood that the steps may proceed in a different logical order or additional or intervening steps may be included without detracting from the invention.

The method 400 begins with forming a molten hot melt at 402 by heating the hot melt adhesive to at or above the softening/melting point of the hot melt. Preferably, a hot melt having a low softening/melting point is used, for example less than 392° F. (200° C.), and the hot melt is heated just to the softening/melting point, although it is within the scope of the invention for hot melt adhesives having higher or lower softening/melting points to be used. Fragrance compounds are volatile compounds, thus higher temperatures will increase the rate and amount of vaporization of the fragrance compounds, diminishing the amount of fragrance in the final mixture.

At 404, a fragrance or mixture of fragrance in liquid form blended with an oil carrier, for example, can be added to the molten hot melt formed at 402. The fragrance can be provided at room temperature to diminish volatilization of the fragrance compounds. The fragrance can also be premixed with a dye to provide the mixture with a color.

At 406, the molten hot melt and fragrance can be mixed to form a homogenous, fragranced hot melt in a mixing chamber. In one example, the mixing chamber comprises a static mixing nozzle. Static mixing nozzles are typically used for polymer melt homogenization in injection molding and extrusion for mixing multiple polymers or colorants. Static mixing nozzles accomplish mixing by the geometric structure of mixing bars that continuously divide and recombine the molten polymer flowing through them. The proper size and number of mixing elements in the static mixing nozzle is a function of the injection flow rate and viscosity of the polymer melt at the operating conditions.

At 408, the fragranced hot melt mixture can be applied as it is ejected from the mixing chamber in molten form through an injector tip directly onto one of the filters 18, 118, 118', 218 and 218' or the bag filter 360, as described above. As the fragranced hot melt cools, it solidifies, forming a fragranced, waxy solid, which emits an odor or scent.

FIG. 9 illustrates a method 500 that may be used alone or in combination with the method 400 of FIG. 8 or the method 600 of FIG. 10, which will be described below. At 502, a mixture of molten hot melt and fragrance is formed, such as described above with respect to the method 400, for example. At 504, the molten mixture can be formed into a stick or other suitable shape and allowed to cure, such as by cooling, for example, and solidify. The solidified sticks can be stored for future use in a glue gun or other suitable applicator. The molten mixture can be formed into sticks using a mold or by extruding the molten mixture and cutting the molten mixture into pieces having a desired length. To apply the fragranced hot melt to one of the filters 18, 118, 118', 218 and 218' or the bag filter 360, the fragranced hot melt stick can be heated to soften the fragrance hot melt stick at 506 using the glue gun, for example, such that it can be applied at 508 to the filter or filter bag as described above.

The solidified mixture formed at 504 can be formed into any suitable shape depending on the hot melt equipment that will be used in forming and applying the molten mixture. Non-limiting examples include sticks, chips and pellets that can be used in hot melt equipment such as glue guns and pail heaters.

Referring now to FIG. 10, a flow chart of a method 600 of making and applying a solid fragrance carrier 32 comprising a polymeric gel as the polymeric matrix and a fragrance is illustrated. The sequence of steps depicted for this method and the proceeding methods are for illustrative purposes only, and is not meant to limit any of the methods in any way as it is understood that the steps may proceed in a different logical order or additional or intervening steps may be included without detracting from the invention.

The method 600 begins at 602 with preparing a polymeric gel in liquid form for mixing with a fragrance and optionally additional additives, such as a colorant, for example at 604. At 606 the polymeric gel and fragrance can be mixed according to any suitable manner, such as using static mixing nozzles, for example, to form a liquid fragranced gel. At 608 the polymeric gel and fragrance mixture can be applied to a substrate, such as a filter or filter bag. The mixture can be applied to a substrate through an injector tip, such as may be coupled with a static mixing nozzle system. In another example, the mixture can be applied using a glue gun that includes a heat pot. At 610 the polymeric gel and fragrance mixture can be cured to solidify the polymeric gel matrix such that the gel adhesively bonds to the substrate and maintains its shape and form as applied to the substrate. Non-limiting examples of curing include cooling to a predetermined temperature or the application of heat or ultraviolet light. As the fragranced polymeric gel cures, it solidifies, forming a fragranced, rubbery solid, which emits an odor or scent.

The polymeric gel can be mixed with a fragrance, cured, stored for later use and then re-heated for application to a substrate in a manner similar to that described above for the hot melt with respect to the method 500 of FIG. 9. In the case of a polymeric gel, a liquid mixture of the polymeric gel and a fragrance can be formed, such as described in the method 600 of FIG. 10 and then the mixture can be formed into a stick or other suitable shape and cured to solidify the material. The solidified sticks can be stored for future use in a glue gun or other suitable applicator. The liquid polymeric gel and fragrance mixture can be formed into sticks using a mold or by extruding the mixture and cutting the mixture into pieces having a desired length. To apply the fragranced polymeric gel to one of the filters 18, 118, 118', 218 and 218' or the bag filter 360, the fragranced polymeric gel stick can be heated to soften the fragrance polymeric gel stick using the glue gun, for example, such that it can be applied to the filter or filter bag as described above.

The solid fragrance carrier described herein can be used with vacuum cleaner filters and bag filters to provide a pleasant scent or aroma to the air that is exhausted from the vacuum cleaner during cleaning of a surface. The solid fragrance carrier can easily be applied to filters and bag filters that have already been manufactured. Alternatively, the solid fragrance carrier can easily be added to the production process to incorporate the solid fragrance carrier as the filters and bag filters are being manufactured. The solidified hot melt or wax acts as a solid carrier for the fragrance, which is emitted from the solid carrier over time. The fragrance emitted from the solid carrier can be carried with the airstream of the vacuum cleaner as it is exhausted from the vacuum cleaner to provide the exhaust air with a desired aroma.

Because the solid fragrance carrier is formed from an adhesive material, the solid fragrance carrier can be applied to one or more substrates within the airflow system of the vacuum cleaner to provide a fragrance to the airstream flowing through and being exhausted from the vacuum cleaner in such a manner that the solid fragrance carrier provides little to no increase in the resistance to the airstream in the airflow system. Systems which require a container to hold a fragrance carrier within the airstream can increase the resistance to the airstream flow through the system, which can result in decreased suction power and/or require the use of a larger suction motor. The adhesive solid fragrance carrier described herein can be placed within the airflow system, such as on or adjacent the filter frame or on a non-porous portion of the filter bag, so that the solid fragrance carrier does not restrict the airstream.

Forming the solid fragrance carrier using the static mixing nozzles provides a homogenous mixture of a fragrance and polymer matrix that does not require applying high heat to the fragrance and polymeric matrix to achieve a homogenous mixture in a shorter amount of time. Less heat decreases the amount of fragrance lost during production due to volatilization of the fragrance, requiring the use of less fragrance, which decreases costs. In addition, heating can also change the fragrance character, which may not be desirable. More efficient mixing with a static mixing nozzle can also reduce the overall contact time of the solid fragrance carrier and fragrance with heat, decreasing the risk of charring of the material from high temperatures or extended exposure to high temperatures.

In addition, the solid fragrance carrier can be applied as it is emitted from the static mixing nozzle without additional heating, which can further decrease volatilization and loss of the fragrance. Reheating the solidified fragranced hot melt or polymeric gel for application to a filter or filter bag can result in additional volatilization and loss of fragrance, decreasing the strength and duration of the scent or aroma emitted from the solidified hot melt.

To the extent not already described, the different features and structures of the various embodiments may be used in combination with each other as desired. That one feature may not be illustrated in all of the embodiments is not meant to be construed that it cannot be, but is done for brevity of description. Thus, the various features of the different embodiments may be mixed and matched as desired to form new embodiments, whether or not the new embodiments are expressly described.

While the invention has been specifically described in connection with certain specific embodiments thereof, it is to be understood that this is by way of illustration and not of limitation. Reasonable variation and modification are possible within the scope of the forgoing disclosure and drawings without departing from the spirit of the invention which is defined in the appended claims.

What is claimed is:

1. A filter for filtering an airstream in a vacuum cleaner, the vacuum cleaner having a suction source for drawing the airstream from a surface to be cleaned to a debris collector for collecting dirt and debris carried by the airstream, the filter comprising:
   a frame with an edge defining an open area through which air may pass;
   a filter media mounted to the frame and covering the open area; and
   an adhesive comprising a fragrance-containing polymeric matrix adhesively bonded directly to the frame adjacent the edge of the frame and directly to the filter media adjacent the edge of the frame to join the frame with the filter media;
   wherein the filter media is secured to the frame by the adhesive bond formed by the fragrance-containing polymeric matrix.

2. The filter of claim 1 wherein the fragrance-containing polymeric matrix comprises at least one of a hot melt adhesive, a wax, or a polymeric gel characterized by an ability to be in liquid form prior to curing and in solid form upon curing, wherein the fragrance-containing polymeric matrix is applied to the filter in liquid form, prior to curing.

3. The filter of claim 1 wherein the edge of the frame and the fragrance-containing polymeric matrix together define the open area through which air may pass, wherein the open area is free of the fragrance-containing polymeric matrix.

4. The filter of claim 1 wherein the fragrance-containing polymeric matrix includes a dye to provide a visual indicator of the presence of the fragrance-containing polymeric matrix.

5. A filter bag for use in a vacuum cleaner, the vacuum cleaner having a suction source for drawing an airstream from a surface to be cleaned to the filter bag for collecting debris carried by the airstream, the filter bag comprising:
   at least one non-porous portion;

porous walls made from a porous material and defining an interior storage space such that dirt and debris entrained in the airstream are filtered out of the airstream and collected within the interior storage space of the filter bag as the airstream passes through the porous walls; and an adhesive comprising a fragrance-containing polymeric matrix adhesively bonded to the at least one non-porous portion of the filter bag.

6. The filter bag of claim 5 wherein the fragrance-containing polymeric matrix is adhesively bonded to the at least a portion of the porous material.

7. The filter bag of claim 5 wherein the non-porous portion comprises at least one of a fold or a seam of the filter bag.

8. The filter bag of claim 5 wherein the fragrance-containing polymeric matrix comprises at least one of a hot melt adhesive, a wax, or a polymeric gel characterized by an ability to be in liquid form prior to curing and in solid form upon curing, wherein the fragrance-containing polymeric matrix is applied to the filter bag in liquid form, prior to curing.

9. A method of forming a solid fragrance carrier on a filter element in a vacuum cleaner comprising:

mixing a liquid polymeric gel with a liquid fragrance to form a fragranced gel;

curing the fragranced gel to form a solidified fragranced gel;

subsequent to forming the solidified fragrance gel, heating the solidified fragranced gel to soften the solidified fragrance gel;

applying the softened fragranced gel to a filter element for a vacuum cleaner; and curing the fragranced gel to solidify the fragranced gel on the filter element such that the fragranced gel adhesively bonds to the filter element.

10. The method of claim 9 wherein the filter element comprises a filter or a filter bag.

11. The method of claim 9 wherein the mixing comprises mixing the liquid polymeric gel with the liquid fragrance in a static mixing nozzle.

12. The method of claim 9 wherein the curing the fragranced gel comprises at least one of cooling the fragranced gel, applying heat, or applying ultraviolet light to the fragranced gel.

* * * * *